US008002785B2

(12) United States Patent
Weiss et al.

(10) Patent No.: US 8,002,785 B2
(45) Date of Patent: Aug. 23, 2011

(54) LANCING APPARATUS FOR PRODUCING A PUNCTURE WOUND

(75) Inventors: Thomas Weiss, Mannheim (DE); Richard Forster, Fensterbach (DE); Peter Sachsenweger, Zeitlarn (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 281 days.

(21) Appl. No.: 11/681,371

(22) Filed: Mar. 2, 2007

(65) Prior Publication Data

US 2007/0233167 A1  Oct. 4, 2007

Related U.S. Application Data

(63) Continuation of application No. PCT/EP2005/009089, filed on Aug. 23, 2005.

(30) Foreign Application Priority Data

Sep. 4, 2004  (DE) .......................... 10 2004 042 886

(51) Int. Cl.
*A61B 17/14* (2006.01)
*A61B 17/32* (2006.01)

(52) U.S. Cl. ...................................................... 606/181

(58) Field of Classification Search .................. 606/181, 606/182, 183, 185, 186, 184; 600/583, 578; 206/364–366; 227/175.1
See application file for complete search history.

(56) References Cited

U.S. PATENT DOCUMENTS

| 5,370,629 | A  | * | 12/1994 | Michel et al. ................. 604/207 |
| RE35,803 | E | * | 5/1998 | Lange et al. .................. 606/182 |
| 6,228,100 | B1 | * | 5/2001 | Schraga ........................ 606/183 |
| 6,530,892 | B1 |  | 3/2003 | Kelly |
| 6,887,254 | B1 | * | 5/2005 | Curie ............................ 606/181 |
| 7,223,276 | B2 | * | 5/2007 | List et al. ...................... 606/181 |
| 2002/0111587 | A1 | * | 8/2002 | Hommann et al. ........... 604/211 |
| 2002/0120216 | A1 |  | 8/2002 | Fritz et al. |
| 2003/0199911 | A1 |  | 10/2003 | Boecker et al. |
| 2004/0230216 | A1 | * | 11/2004 | Levaughn et al. ............. 606/181 |
| 2005/0149089 | A1 | * | 7/2005 | Trissel et al. ................. 606/181 |
| 2005/0234494 | A1 | * | 10/2005 | Conway et al. ............... 606/181 |

(Continued)

FOREIGN PATENT DOCUMENTS

DE   100 22 720   11/2001

(Continued)

*Primary Examiner* — Todd E Manahan
*Assistant Examiner* — Jocelin C Tanner
(74) *Attorney, Agent, or Firm* — Bose McKinney & Evans LLP (57) ABSTRACT

A lancing apparatus for producing a puncture wound, comprising a magazine holder for a lancet magazine with a plurality of lancets. The lancet drive comprises a drive spring, a tensioning device for tensioning the drive spring and a push rod, the push rod being adapted for coupling to a lancet located in the lancet magazine and being adapted for moving at high velocity, together with a lancet coupled thereto, by means of lancet drive during a puncture and retraction movement to produce a puncture wound. A magazine advancing mechanism is provided for advancing the lancet magazine in such a manner that the lancets stored therein can be coupled to the push rod one after the other. According to exemplary embodiments, the lancet drive is not mechanically coupled to the magazine advancing mechanism whereby a plurality of puncture wounds can be produced using the same lancet a plurality of times. The lancing apparatus compromises an actuating element for actuating the magazine advancing mechanism independently from the lancet drive, in particular for actuating it independently from the tensioning device.

16 Claims, 4 Drawing Sheets

U.S. PATENT DOCUMENTS

2006/0235454 A1 * 10/2006 LeVaughn et al. ............ 606/181

FOREIGN PATENT DOCUMENTS

| | | |
|---|---|---|
| DE | 100 47 419 | 4/2002 |
| EP | 1 384 438 | 1/2004 |
| WO | WO01/00090 * | 1/2001 |
| WO | WO 01/00090 | 1/2001 |
| WO | WO 02/36010 | 5/2002 |
| WO | WO 03/071940 | 9/2003 |

* cited by examiner

LANCING APPARATUS FOR PRODUCING A PUNCTURE WOUND

RELATED APPLICATIONS

This is a continuation application of International Application PCT/EP2005/009089, filed Aug. 23, 2005, which claims priority to DE 10 2004 042 886.7, filed Sep. 4, 2004, which are hereby incorporated by reference in their entirety.

BACKGROUND

The present invention relates to a lancing apparatus for producing a puncture wound, in particular for obtaining a blood sample, which is to be analyzed for medical purposes. It comprises a magazine holder for a lancet magazine with a plurality of lancets, a lancet drive with a drive spring, a tensioning device for tensioning the drive spring, and a push rod, the push rod being adapted for coupling to a lancet located in the lancet magazine and the push rod being adapted for moving at high velocity, together with a lancet coupled thereto by means of the lancet drive during a puncture and retraction movement for producing a puncture wound. The apparatus also includes a magazine advancing mechanism for advancing the lancet magazine in such a manner that the lancets stored therein can be coupled to the push rod one after the other. The present invention also relates to a blood sampling system comprising such a lancing apparatus and a lancet magazine adapted thereto and including a plurality of lancets.

For sampling a small quantity of blood from a body part (usually from a finger or earlobe) for analytic-diagnostic purposes, lancets are used, which are pierced into the corresponding body part for producing a puncture wound. Blood sampling systems have been available for some time, which comprise a lancing apparatus and associated lancets specially tailored for the particular lancing apparatus. A lancet drive for piercing the lancet mechanically into the skin is located in a housing of the lancing apparatus.

Lancet devices have to fulfill difficult and partially contradictory requirements for minimal pain, simple operation, compact structure, and cost-effective construction. Extensive development work has been performed to fulfill these requirements to the extent possible. One direction of the development efforts has gone toward offering the user more comfort. Simple and comfortable operation is important, in particular, for diabetics, who have to check their blood glucose level frequently to be able to keep it within specific limits by insulin injections. In this context, the usage comfort of the systems is of very high medical significance, because the regular self-checking ("home-monitoring") of blood sugar significantly reduces the risk of grave long-term damage of diabetes mellitus (e.g., retinopathies, which may result in blindness), and any improvement in operating comfort increases the willingness of the patients to perform regular self checking.

One possibility for increasing the comfort and making the operation of a lancing apparatus easier comprises the use of lancet magazines containing a plurality of lancets and adapted to be inserted into a magazine holder of a lancing apparatus. Thereby, the insertion of individual lancets, which is difficult, in particular for sick or frail people whose manual dexterity is restricted, is no longer required.

A blood sampling system having a drum-shaped revolver magazine, which contains 10 lancets located on a ring, is described in DE 10022720 A1. After each puncture, the magazine is advanced automatically, i.e., the magazine of the lancing apparatus is transported into the next position with a fresh lancet. A revolver magazine having a plurality of lancets located on a ring is also used in the blood sampling system described in EP 1384438 A1, which corresponds to U.S. patent application Ser. No. 10/445,606, no statements being made about its advancing.

A blood sampling system equipped with a lancet magazine is also described in WO 01/00090 A1. The system comprises a mechanism for automatic step-by-step advancement of the magazine. It is considered advantageous that a fresh lancet is thus used automatically for each new puncture. This applies similarly to U.S. Pat. No. 6,228,100. It teaches different configurations, by which an unused lancet, which is next in line, is brought into the usage position after each triggering of the lancet drive. The reuse of used lancets is thus prevented.

WO 03/071940 A1 and U.S. Pat. No. 6,530,892 describe lancet systems and consider it favorable that in each case the lancet magazine is advanced between two puncture steps in such a manner that each time a fresh lancet is made available.

In spite of these substantial development efforts, up to this point, lancing apparatuses comprising lancet magazines have not established themselves on the market. Therefore, there is a need to provide a magazine lancing apparatus which is better accepted by users.

SUMMARY OF THE INVENTION

Embodiments of the present invention provide a lancet system in which the lancet drive is not coupled to the magazine advancing mechanism. The lancing apparatus comprises an actuating element for actuating the magazine advancing mechanism independently from the lancet drive, in particular, for actuating it independently from the tensioning device.

The developments of blood lancet systems known in the art are based on the conventional wisdom that it is advantageous for the construction and use of magazine blood lancet systems if the magazine is always advanced between two punctures and, accordingly, a new blood lancet is available in each case. Therefore, the advancing mechanism of the magazine is coupled to the lancet drive in such a manner that the magazine advancing occurs alternately with the puncture movements in an automatic and compulsory manner. The coupling is typically mechanical. In the device disclosed in U.S. Pat. No. 6,530,892, the coupling is implemented in an electronic controller of the system functions.

The inventors have found that the relatively complex coupling construction is neither necessary nor especially advantageous for practical handling. To the contrary, in the field of home monitoring, the handling is simplified and a simplified construction is simultaneously achieved if the functions of the lancet drive and the magazine advancing mechanism are separated. It is easily possible to spatially separate the functions of "setting the puncture depth" and "advancing the lancet magazine" and to localize them in such a manner that intuitive operation is possible: puncture depth setting at the front end of the device in proximity to the exit opening of the lancet; magazine advancing mechanism at the rear end, in particular combined with the same actuating element used for tensioning the lancet drive.

The described and further advantages are in particular achieved if, in addition, at least a part of the preferred features are used which are explained hereafter on the basis of an exemplary embodiment. Significant additional cost savings are achieved if the user himself can determine how frequently he advances the magazine and thus brings a new lancet into use.

Further details and advantages of the present invention are explained hereafter on the basis of an exemplary embodiment with reference to the attached figures. The features illustrated therein can be used individually or in combination to provide preferred embodiments of the present invention.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

Corresponding reference numerals are used to indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
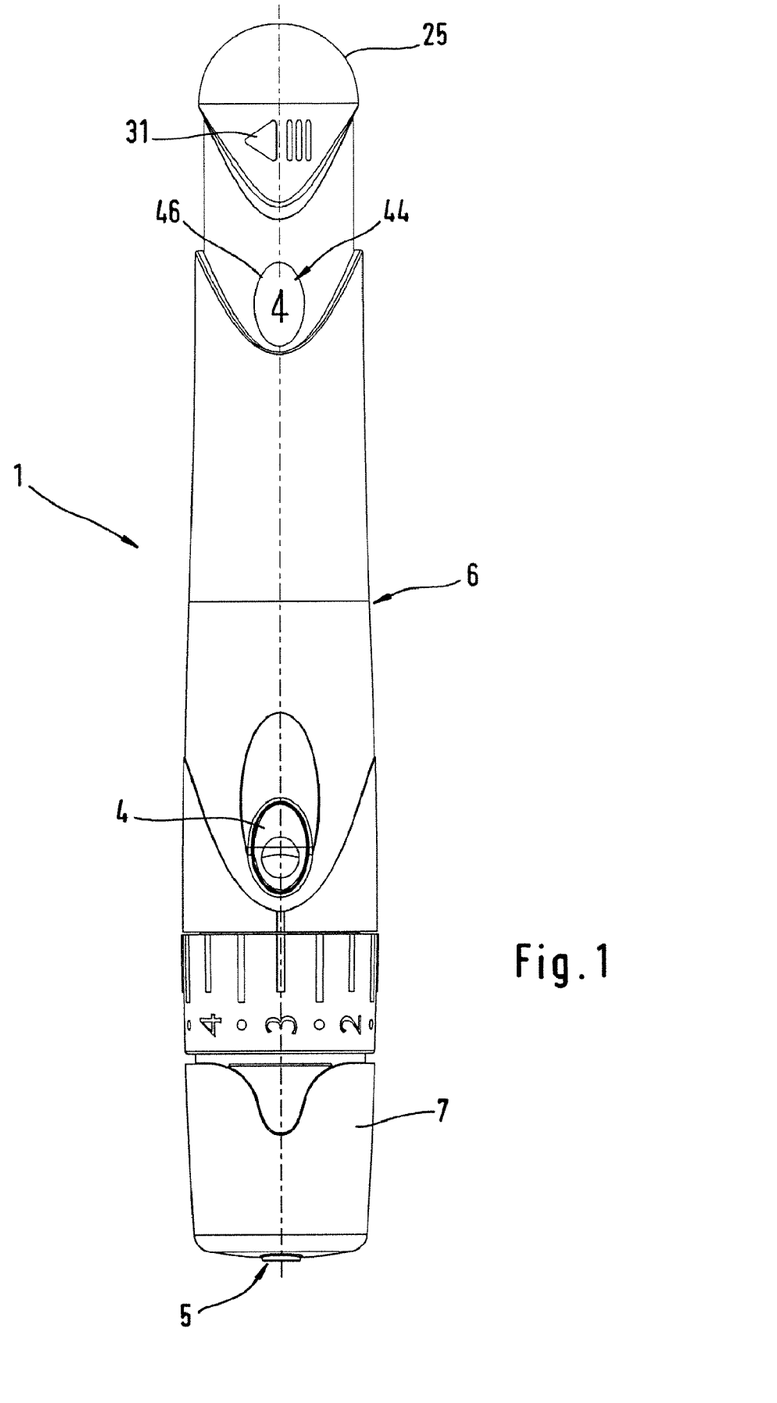
FIG. 1 shows a lancing apparatus according to the present invention in a side view.
Figure 2:
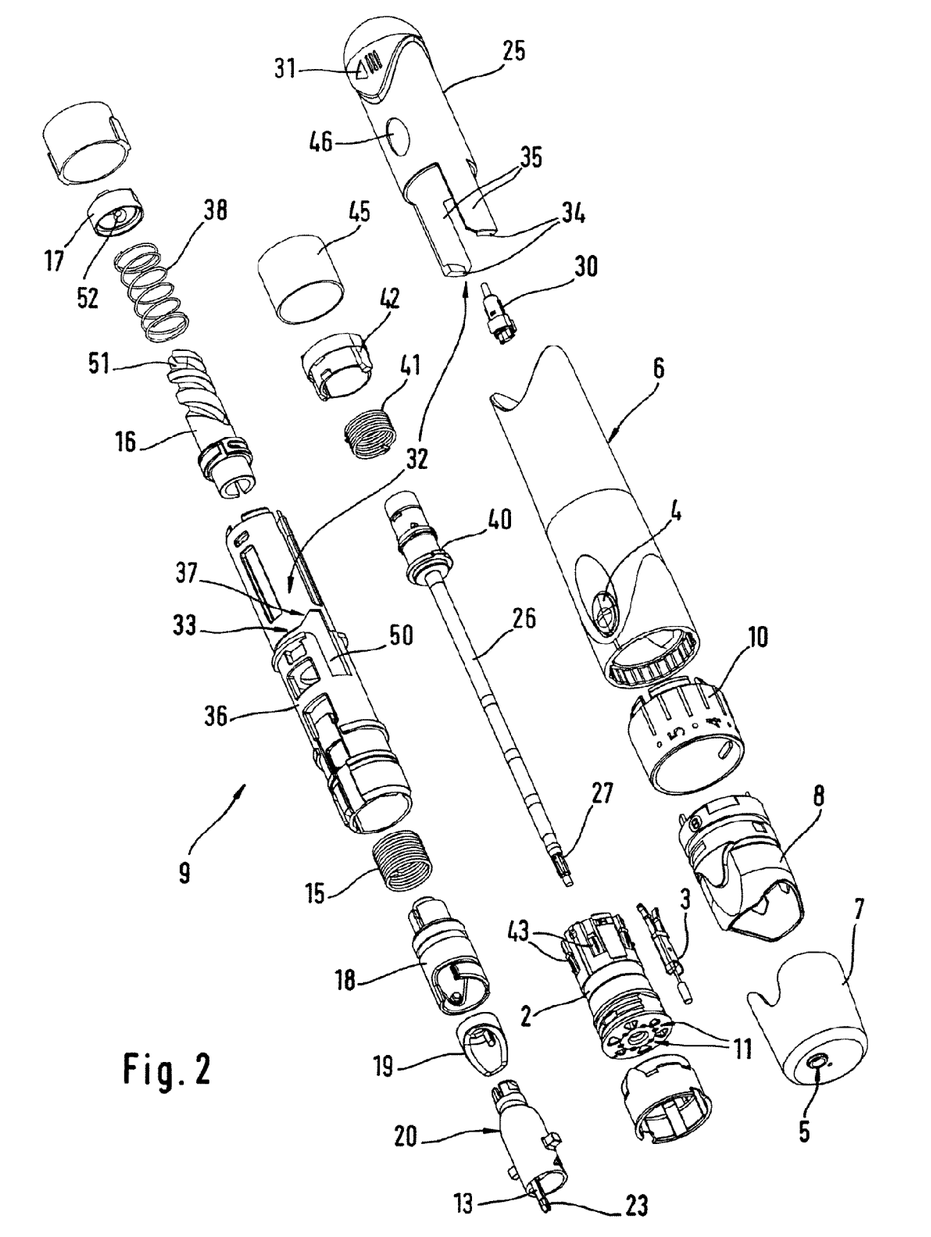
FIG. 2 shows the lancing apparatus in an exploded perspective view.

The blood sampling system shown in FIGS. 1 and 2 comprises a lancing apparatus 1 and a lancet magazine 2, adapted thereto and including a plurality of lancets 3. It is used for generating a puncture wound for sampling blood for diagnostic purposes. By pressing a trigger element 4, the movement of a lancet drive 9 of the lancing apparatus 1 is started so that the tip of a lancet 3 exits at high velocity from an exit opening 5 of the housing 6. In the exemplary embodiment shown, the exit opening 5 is located at a cap 7 belonging to the housing 6, which encloses a lancet magazine 2 inserted into a magazine holder 8. A puncture depth adjustment ring 10 is used for adjusting a puncture depth which is optimal for minimum pain and the amount of blood obtained upon a puncture.

As FIG. 2 shows, the lancet magazine 2 is implemented as a (drum-shaped) revolver magazine and contains a plurality of preferably six lancets 3. The lancets 3 are positioned in annularly located lancet holders of the lancet magazine 2. A lancet opening 11 is assigned to each lancet holder, adapted to be aligned with the exit opening 5 in a coupling position by rotating the lancet magazine 2. An insertion opening 12 (see FIG. 3) for a push rod 13 of the lancet drive, adapted to be coupled to one of the lancets 3 in the coupling position, is located opposite each lancet opening 11.

The lancet drive 9 comprises a drive spring 15, a tensioning device 16, 17 for tensioning the drive spring 15, and the push rod 13, the push rod 13 being adapted for moving at high velocity, together with a lancet 3 coupled thereto, driven by the lancet drive 9, in such a manner that a puncture and retraction movement is executed.

As can be appreciated from FIG. 2, further elements of the lancet drive 9 are a drive rotor 18 adapted to be driven by the drive spring 15 and an output-side coupling mechanism 19, 20, by which, in a forward movement phase of the lancet drive, a rotational movement of the drive rotor 18 is converted into a translational movement of the push rod 13 and thereby, into a puncture movement of the lancet 3.

The tensioning device includes a rotationally-movable tensioning rotor 16, on which the end of the drive spring 15 facing away from the drive rotor 18 is supported. The tensioning rotor 16 is adapted to rotate, while rotation of the drive rotor 18 is blocked, in the same rotational direction in which the drive rotor 18 rotates during the forward movement phase, thereby tensioning the drive spring 15. During the forward movement phase, the tensioning rotor 16 is locked against backwards movement, so that, after release of the blocking, the drive rotor 18 performs a rotational movement which is converted into a translational movement of the push rod 13. The drive rotor rotates during a work cycle, i.e., during a use of the device, through a total rotational angle range of 360°.

The tensioning device is actuated by a rotary-slide-transmission 51, 52, which cooperates with an actuating element 25 for tensioning the drive spring 15 when the actuating element 25 is pressed down. As FIG. 2 shows, the rotary-slide-transmission is formed by a cam 51 in the form of a peripheral double groove on the tensioning rotor 16 and two control pins 52 of the tensioning sleeve 17, which travel along the cam 51 when the actuating element 25 is pressed down.

A lancet drive of this type is described in EP 1384438 A1, which corresponds to U.S. patent application Ser. No. 10/445,606, wherein the expression OWADAC (One Way Alternating Drive and Cocking) is used. The content of this document is incorporated in the disclosure of the present application by reference in regard to further features and functions of the lancet drive.

As already noted, the lancet magazine 2 has an insertion opening 12 diametrically opposite each lancet opening 11. The push rod 13 can be pushed through the insertion opening 12 to couple to a lancet 3 in the lancet magazine 2. The corresponding position of the lancet holder with a lancet 3 is referred to as the coupling position. The thickened head part 23 of the push rod 13 is coupled in a formfitting manner to the lancet 3, so that it remains connected to the push rod 13 during the puncture and retraction movement. Further details and alternative embodiments of a suitable coupling mechanism are described in WO 02/36010 A1, which corresponds to U.S. patent application Ser. No. 10/415,577, which is hereby incorporated in the disclosure of the present application by reference.

The rotation of the lancet magazine 2 by a rotation step, in which the next lancet 3 is brought into the next coupling position, is referred to as advancing or indexing and is achieved using a magazine advancing mechanism, which is described in greater detail hereafter.

The magazine advancing mechanism 14 is not mechanically coupled to the lancet drive. Rather, the lancing apparatus 1 has an actuating element 25 for actuating the magazine advancing mechanism independently from the lancet drive, in particular independently from the tensioning device 16, 17. Thus, the user can determine himself how frequently he advances the magazine and thus brings a new lancet into use.

Figure 3:
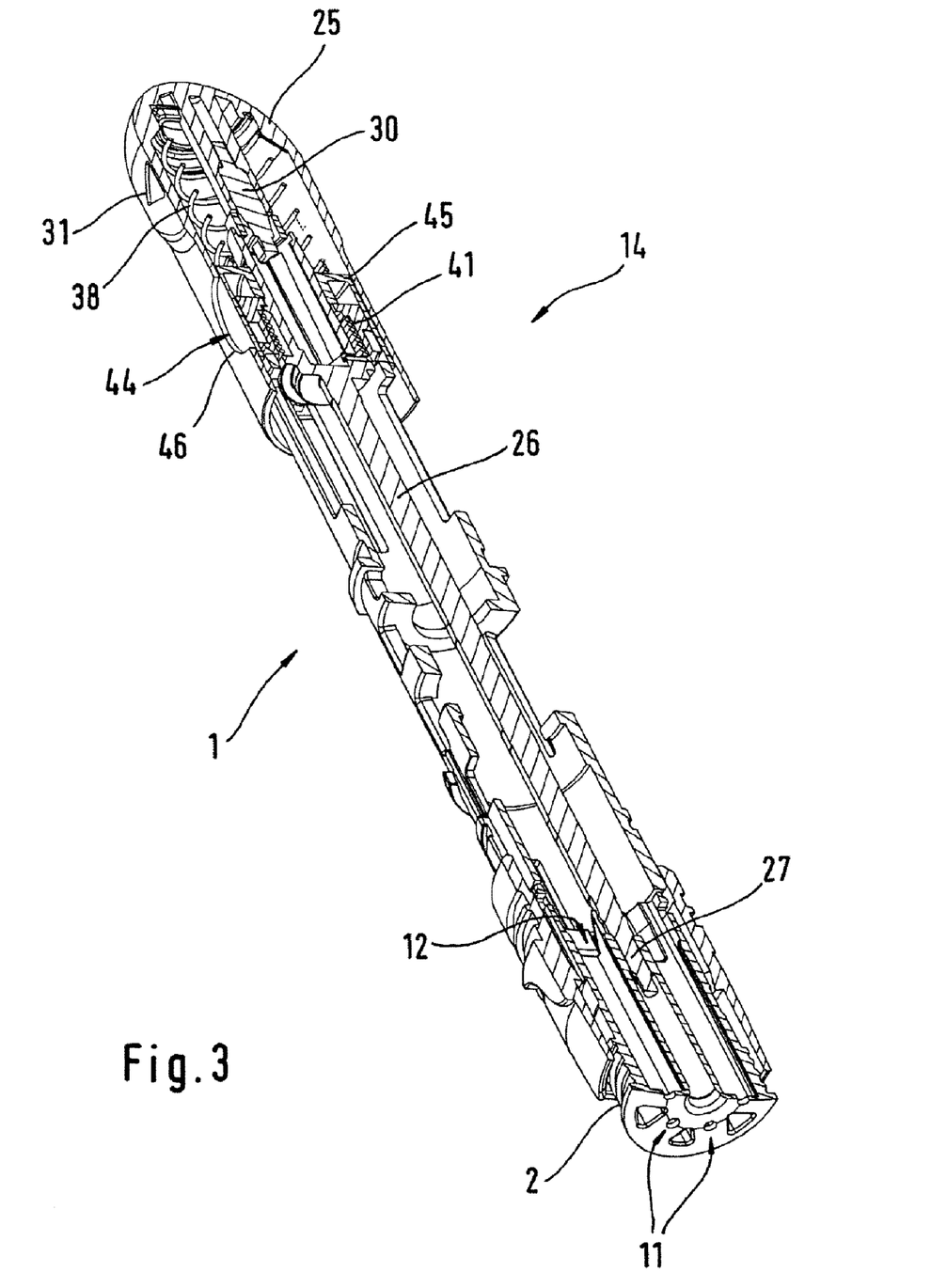
FIG. 3 is a perspective view of the lancing apparatus with portions of the housing cut away.
Figure 4:
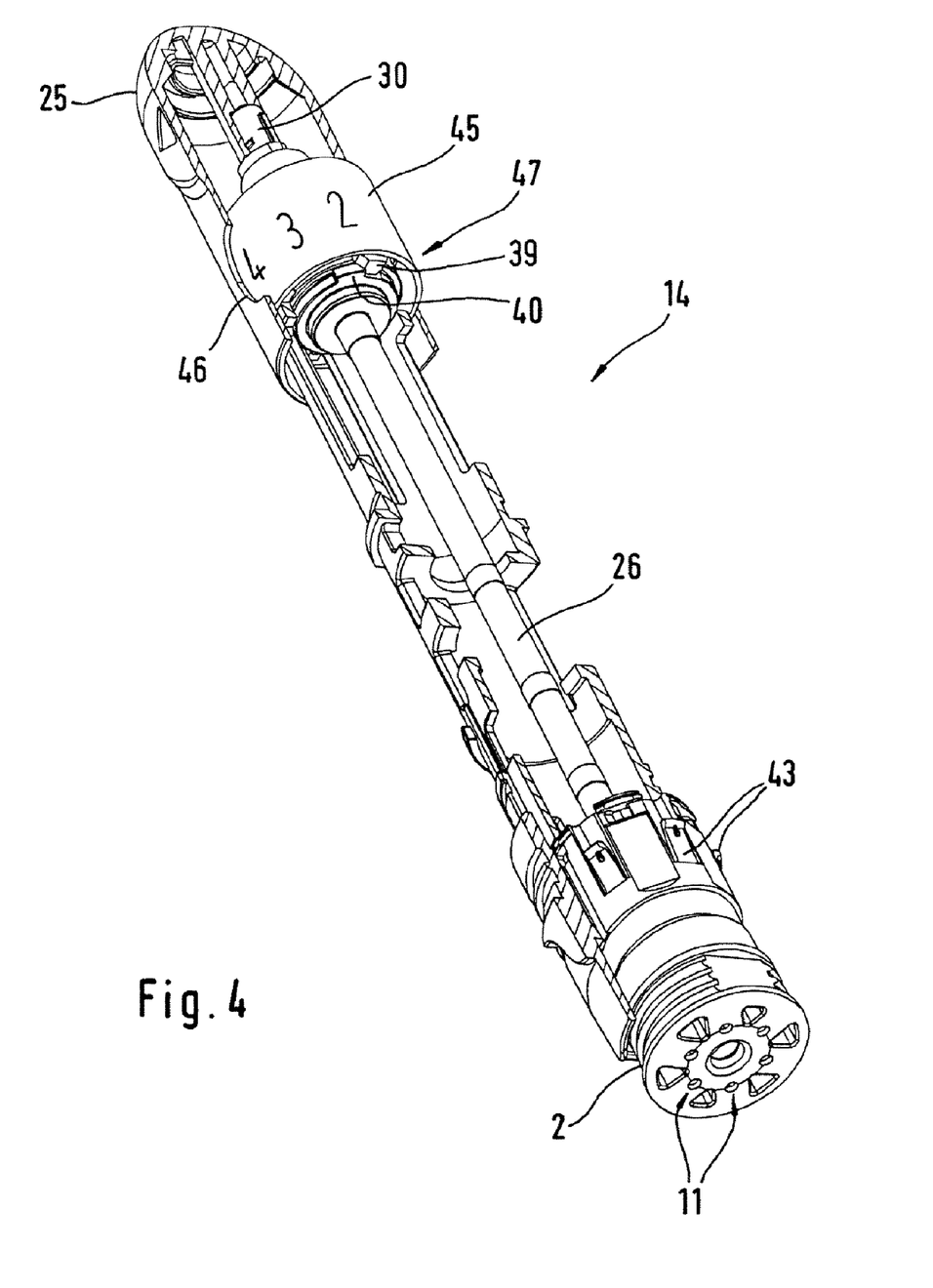
FIG. 4 is a perspective view similar to FIG. 3, but illustrating some parts of the lancing apparatus in a full rather than sectional view.

The elements of the magazine advancing mechanism are shown in the assembled state in FIGS. 3 and 4, in which the lancet drive is not shown for the sake of better visibility. The magazine advancing mechanism 14 includes an axle 26 for plugging on and for rotating the lancet magazine 2. The axle 26 has a head 27 having a profiled ring to ensure a rotationally fixed coupling to the lancet magazine 2. The magazine advancing mechanism is actuated by a rotational movement of the actuating element 25. This rotational movement is transmitted by a coupling part 30 to the axle 26. Alternatively, the magazine advancing mechanism can also be actuated by a translational movement of the actuating element, which is converted, for example by a rotary-slide-transmission, into a rotational movement of the axle 26.

The magazine advancing mechanism 14 is implemented in such a manner that the lancet magazine 2 is adapted for advancing only in one direction. For this purpose, it includes a direction-switched coupling by means of the coupling part 30, which is positioned between the axle 26 and actuating element 25. The direction-switched coupling 30 is preferably a pawl freewheel, in particular, a ratchet. A rotational movement of the actuating element 25 can only be transmitted in one direction to the axle 26 by the direction-switched coupling 30. An arrow-shaped profiled marking 31 is fixed to the actuating element 25 to indicate the correct rotational direction to the user.

The magazine advancing mechanism comprises rotational step limiting means 32 in order that the lancet magazine 2 is rotated upon each actuation of the magazine advancing mechanism only so far that the next lancet 3 reaches its coupling position with the push rod 13 (i.e., the "active position"). These rotational step limiting means 32 are explained hereafter with reference to FIG. 2.

In the exemplary embodiment shown, the rotational step limiting means 32, which limits the rotational advancement of the lancet magazine to the extent that the next successive unused lancet is transferred to the active position, is implemented by a cam mechanism having a cam 33 and a cam traveler 34. The cam 33 is formed by a recess rotationally fixed in relation to the housing. It extends over a sufficiently small angular range around the circumference, namely less than twice a rotational step (rotational segment) of the magazine advancing mechanism 14. To avoid tilting torques, two recesses 33 of this type and two cam travelers 34 are provided in diametrically opposing positions. Since the lancet magazine of the exemplary embodiment shown has six lancet holders, one rotational step or segment is 60°. The recess 33 therefore preferably extends only over a peripheral angular range of 70 to 90°, i.e., significantly less than 120°.

One of the cam travelers 34, which are each located at the end of two guide arms 35 of the actuating element 25, engages with each recess 33. During a rotational movement of the actuating element 25, the cam travelers 34 are guided by the respective recess 33 until they stop at the end of the recess 33, whereby a rotation of the actuating element 25 beyond the permitted range is precluded. In the simplest case, the cam 33 can be positioned in the housing 6 itself. In the exemplary embodiment shown, the cam is located in a sleeve 36 which is rotationally fixed connected to the housing.

As shown in FIG. 2, the cam 33 does not run exactly in circumferential direction along its complete length. Rather, it is slightly inclined in a starting section. The actuating element 25 is moved slightly in the axial direction at the beginning of a rotational movement and pressed against the axle 26 due to the inclination 37. The axle 26 is thereby engaged with the actuating element 25 by the coupling part 30, so that a rotational movement of the actuating element 25 can be transmitted to the axle 26.

The actuating element 25 is reset into its original position before the next actuation of the magazine advancing mechanism. To this end the user can manually rotate the actuating element 25 back. To make the handling of the lancing apparatus 1 as simple as possible, in the exemplary embodiment shown this occurs automatically by means of a spring 38. The spring 38 can be a torsion spring, which counteracts a rotational movement of the actuating element. Preferably, a compression spring is used, which is compressed in the axial direction during the spring movement during a rotation of the actuation element. Due to the inclination 37 of the cam 33, resetting of the actuating element 25 is made easier for a user by the force of the spring 38 acting in axial direction.

As shown in FIG. 4, the magazine advancing mechanism 14 includes a rotation limitation device 40, restricting the rotation of the lancet magazine to less than 360°. This measure has the advantage that a lancet 3, which was already used some time ago, is not unintentionally taken for a fresh lancet 3 and used again. Several days may pass under certain circumstances between the use of the first lancet 3 and the last lancet of a lancet magazine 2. In such a long period of time, pathogens and spores originating from the environment can multiply to such an extent on a used lancet 3 that there is a health danger even if the lancet 3 is used by the same person. In contrast, there is practically no danger of infection in the case of double or triple use of a lancet in a period of a few hours, which is practiced by many diabetics in the course of their regular self-monitoring of the blood sugar content.

In the exemplary embodiment shown, the rotation limitation device 47 is implemented by a stop element 40 located on the axle. The stop element engages a stop 39 rotationally fixed in relation to the housing 6. In the simplest case, the stop 39 can be positioned at the housing 6 itself. In the exemplary embodiment shown, the stop is part of a sleeve enclosing the axle 26.

Upon each exchange of the lancet magazine 2, the axle 26 rotates back into its original position, driven by a restoring spring 41 shown in FIGS. 2 and 3, which is preferably under pre-tension. As a result, there is no engagement of the rotation limitation device 47 until the axle 26 and thus also the lancet magazine 2 have been rotated far enough to allow use of all lancets 3. The restoring spring is a torsion spring 41 which is located around the axle 26. One end of this spring is supported on the axle 26 and the other end is supported on a support sleeve 42 which is connected rotationally fixed to the housing 6.

The restoring spring 41 is increasingly tensioned upon each actuation of the magazine advancing mechanism, i.e., upon each rotational angle step or segment of the lancet magazine 2. A reverse motion locking device 43 prevents backward rotation of the lancet magazine 2 when a coupling position has been reached. Thus, while a lancet may be used several times, as described above, once the lancet magazine has been advanced, the used lancet is prevented from returning to the active position. In the exemplary embodiment shown, the reverse motion locking device 43 is implemented by spring legs on the outer surface of the lancet magazine 2, which engage with beveled recesses (not shown) of the magazine holder 8. The slopes of the recesses are oriented so that the spring legs can slip along the slope face and out of the recesses upon a rotation of the lancet magazine 2 in the correct rotational direction, while a rotation in the opposite direction is prevented by a steep edge or an undercut which engage with the spring legs. When a lancet magazine is removed from the magazine holder, the reverse motion locking device 43 is disengaged, whereby the axle 26 is automatically rotated back into its starting position by the restoring spring 41.

As can be seen in particular in FIGS. 1 and 2, the lancing apparatus 1 has a display unit 44 for displaying the number of unused lancets of a lancet magazine positioned in the magazine holder. The display unit comprises a marking ring 45, which has markings, in particular, numbers, on an exterior side facing toward a housing window 46. Each marking is assigned to a number of unused lancets of the lancet magazine. An actuation of the magazine advancing mechanism causes a rotational angle step of the marking ring 45 in relation to the housing window 46, whereby a marking of the marking ring 45 becomes visible in the housing window 46 which is assigned to the next smaller number of unused lancets 3.

Instead of numbers, bars of varying length extending around the circumference can also be displayed on the marking ring. Then, a user can recognize the number of unused lancets 3 on the basis of the number of bars visible in the window.

Instead of a window 46, through which only a part of the exterior side of the marking ring 45 is visible, a housing construction in which the entire exterior side of the marking ring 45 is visible can also be chosen. Thus, a housing marking, such as an arrow, can indicate which of the visible markings of the marking ring 45 indicates the number of unused lancets. The housing window 46 provided in the exemplary embodiment shown is a housing marking, like an arrow, for displaying which of the visible markings of the marking ring 45 indicates the number of unused lancets.

The marking ring 45 is preferably rotationally fixed to the axle 26. Each rotational angle step (or segmented turn) of the lancet magazine 2 is thus transmitted to the marking ring 45 and a reliable display is provided thereby.

The display unit 44 can also be implemented in such a manner that instead of the number of remaining unused lancets, the number of used lancets is displayed. In general, any display unit indicating the usage state of the lancets of a magazine fixed in the magazine holder to the user is suitable.

The actuating element 25 has a plurality of actuation functions, which are independent of one another. The magazine advancing mechanism is actuated by a first actuation function. The tensioning device 16, 17 is actuated by a second actuating function. As already noted, in the exemplary embodiment shown the magazine advancing mechanism is actuated by rotating the actuating element 25, and the tensioning device 16, 17 is actuated by pressing it down. Thereby, the number of required actuating elements is reduced to a minimum and the handling is improved.

Rotation of the actuating element 25 during pressing down is prevented by a guide 50 running in the axial direction. Thereby unintended actuation of the magazine advancing mechanism is avoided during the tensioning procedure. The guide 50 is implemented as grooves running in the axial direction in the exemplary embodiment shown. A guide arm 35 of the actuating element 25 engages in each of the grooves. Depending on the actuating function, the cam travelers 34 are thus guided by the cam 33 or the guide groove 50.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

REFERENCE LIST

1 lancing apparatus
2 lancet magazine
3 lancet
4 trigger element
5 exit opening
6 housing
7 cap
8 magazine holder
9 lancet drive
10 puncture depth adjustment ring
11 lancet opening
12 insertion opening
13 push rod
14 magazine advancing mechanism
15 drive spring
16 tensioning rotor
17 tensioning sleeve
18 drive rotor
19,20 coupling mechanism
23 head part of the push rod
25 actuating element
26 axle
27 head of axle
30 coupling part
31 marking
32 rotational step limiting means
33 cam
34 cam traveller
35 guide arm
36 sleeve
37 inclination
38 spring
39 stop
40 stop element
41 restoring spring
42 support sleeve
43 reverse motion locking device
44 display unit
45 marking ring
46 housing window
47 rotation limitation device
50 guide
51,52 rotary-slide-transmission

What is claimed is:

1. A lancing apparatus for producing a puncture wound, comprising:
    a housing a magazine holder disposed in the housing and configured to hold a lancet magazine having a plurality of lancets;
    a lancet drive comprising a drive spring, a tensioning device for tensioning the drive spring, and a push rod which couples to a lancet located in the lancet magazine and moves lancet in a puncture movement and a retraction movement the magazine holder being positioned in front of the lancet drive along the direction of the puncture movement;
    a magazine advancing mechanism for advancing the lancet magazine; and
    an actuating element configured to actuate the magazine advancing mechanism independently from the tensioning device;
    wherein
    the lancets stored in the magazine can be coupled to the push rod one after another;
    the lancet drive is not coupled to the magazine advancing mechanism, whereby the same lancet coupled to the push rod can be driven by the lancet drive in the puncture and retraction movements several times to produce several puncture wounds without advancing the lancet magazine;
    the magazine advancing mechanism is configured to advance the lancet magazine in only one direction; and the magazine advancing mechanism comprises a rotation limitation device for restricting the rotation of the lancet magazine to less than 360°.

2. The lancing apparatus of claim 1, wherein the actuating element is rotatable and the magazine advancing mechanism is actuated by rotating the actuating element.

3. The lancing apparatus of claim 1, wherein the lancet magazine is a revolver magazine.

4. The lancing apparatus of claim 3, wherein the magazine advancing mechanism comprises an axle which couples the actuating element to the lancet magazine.

5. The lancing apparatus of claim 4, wherein the magazine advancing mechanism comprises a unidirectional coupling located between the axle and the actuating element.

6. The lancing apparatus of claim 5, wherein the unidirectional coupling comprises a ratchet.

7. The lancing apparatus of claim 1, wherein the magazine advancing mechanism comprises a restoring spring adapted to be tensioned upon actuation of the magazine advancing mechanism.

8. The lancing apparatus of claim 1, further comprising a display for displaying usage status of the lancets of a lancet magazine inserted into the magazine holder.

9. The lancing apparatus of claim 8, wherein the display comprises a ring having markings on an exterior side thereof, each marking being assigned to a position of a lancet in the lancet magazine, wherein actuation of the magazine advancing mechanism turns the marking ring relative to a housing marking to align the housing marking with one of the markings of the marking ring.

10. The lancing apparatus of claim 9, wherein the ring has numeric markings and the numeric marking that is aligned with the housing marking after the turn corresponds to the number of unused lancets in the magazine.

11. The lancing apparatus of claim 1, wherein the actuating element has at least two independent actuation functions, the magazine advancing mechanism being actuated using a first actuation function and the tensioning device being actuated using a second actuation function of said actuating element.

12. The lancing apparatus of claim 11, wherein one of the two actuating functions is triggered by rotating the actuating element and the other of the two actuating functions is triggered by depressing the actuating element.

13. The lancing apparatus of claim 1, wherein the lancet drive comprises a drive rotor adapted to be driven by the drive spring and an output-side coupling mechanism, wherein, in a forward movement phase of the lancet drive, a rotational movement of the drive rotor is converted into a translational movement of the push rod and thereby into the puncture and retraction movement of the lancet.

14. The lancing apparatus of claim 1, wherein the tensioning device comprises a rotary-slide-transmission that cooperates with the actuating element such that the drive spring is tensioned when the actuating element is depressed.

15. The lancing apparatus of claim 1, wherein the magazine advancing mechanism comprises a transport limitation device which prevents movement of the lancet magazine beyond the lancet which is next in line upon actuation of the magazine advancing mechanism.

16. The lancing apparatus of claim 1, further comprising a blood sampling system.

* * * * *